United States Patent
Youn et al.

(10) Patent No.: US 12,246,053 B2
(45) Date of Patent: Mar. 11, 2025

(54) ENU PHARMACEUTICAL COMPOSITION FOR TREATING OR PREVENTING NEUROPATHIC PAIN

(71) Applicants: You Suk Youn, Suwon-si (KR); Young Jin Choi, Seoul (KR); Sang Ho Lee, Seoul (KR)

(72) Inventors: You Suk Youn, Suwon-si (KR); Young Jin Choi, Seoul (KR); Sang Ho Lee, Seoul (KR)

( * ) Notice: Subject to any disclaimer, the term of this patent is extended or adjusted under 35 U.S.C. 154(b) by 0 days.

(21) Appl. No.: 18/407,894

(22) Filed: Jan. 9, 2024

(65) Prior Publication Data
US 2024/0350573 A1  Oct. 24, 2024

(30) Foreign Application Priority Data
Apr. 23, 2023  (KR) .......................... 10-2023-0053043

(51) Int. Cl.
| | | |
|---|---|---|
| *A61K 36/48* | (2006.01) | |
| *A61K 36/18* | (2006.01) | |
| *A61K 36/73* | (2006.01) | |
| *A61K 36/8969* | (2006.01) | |
| *A61K 36/899* | (2006.01) | |
| *A61P 25/04* | (2006.01) | |
| *A61P 29/00* | (2006.01) | |

(52) U.S. Cl.
CPC .............. *A61K 36/48* (2013.01); *A61K 36/18* (2013.01); *A61K 36/73* (2013.01); *A61K 36/8969* (2013.01); *A61K 36/899* (2013.01); *A61P 25/04* (2018.01); *A61P 29/00* (2018.01); *A61K 2236/331* (2013.01)

(58) Field of Classification Search
CPC .... A61K 36/48; A61K 36/73; A61K 36/8969; A61K 36/899; A61K 2236/331; A61K 36/18; A61P 25/04; A61P 29/00
See application file for complete search history.

(56) References Cited

U.S. PATENT DOCUMENTS

| | | | |
|---|---|---|---|
| 8,784,903 B2 * | 7/2014 | Park ...................... | A61K 36/185 |
| | | | 424/725 |
| 9,327,007 B2 * | 5/2016 | Park ...................... | A23L 33/105 |
| 9,775,870 B2 * | 10/2017 | Park ...................... | A61K 36/428 |

FOREIGN PATENT DOCUMENTS

CN         102014940 B  *  2/2013  ........... A23L 33/105

OTHER PUBLICATIONS

Machine translation of CN-102014940-B, 48 pages. (Year: 2013).*
Korean Decision to Grant a Patent issued in corresponding KR Patent Application No. 10-2023-0053043, dated Aug. 24, 2023, with English translation , 4 pages.
Khan, H. et al., "The antinociceptive activity of Polygonatum verticillatum rhizomes in pain models" Journal of Ethnopharmacology (Feb. 2010) pp. 521-527, vol. 127, issue 2.
Korean Office Action issued in corresponding KR Patent Application No. 10-2023-0053043, dated Jun. 7, 2023, with English translation, 5 pages.

\* cited by examiner

*Primary Examiner* — Aaron J Kosar
(74) *Attorney, Agent, or Firm* — Carter, DeLuca & Farrell LLP; George Likourezos

(57) ABSTRACT

The pharmaceutical composition for treating or preventing neuropathic pain includes *Polygonati rhizoma*, *Sorbus commixta* Hedl., *Geranium nepalense*, and *Glycine Semen Preparata*.

5 Claims, 15 Drawing Sheets

ENU PHARMACEUTICAL COMPOSITION FOR TREATING OR PREVENTING NEUROPATHIC PAIN

CROSS REFERENCE TO RELATED APPLICATION

The present application claims the benefit of and priority to Korean Patent Application No. 10-2023-0053043, filed Apr. 23, 2023, the contents of which are incorporated herein by reference in their entirety.

BACKGROUND

1. Field

The present disclosure herein relates to a pharmaceutical composition for treating or preventing treating or preventing neuropathic pain.

2. Description of the Related Art

Neuropathic pain is pain that occurs due to damage or dysfunction of a nervous system and is caused by abnormalities in the transmission or processing of pain signals in the nervous system. Neuropathic pain can be caused by pressure, entrapment, or damage to a nerve, infection, diseases such as diabetes, multiple sclerosis, or certain medications. Pain is expressed as a burning, stabbing sensation, etc. and is accompanied by paralysis or numbness in the affected area.

Sciatic nerve ligation (SNL) is the ligation of the sciatic nerve, which causes pressure, damage, and inflammation of the nerve fibers. SNL is frequently used to induce neuropathic pain in animal models. This pain is characterized by hypersensitivity to stimuli that do not normally cause pain (allodynia) and hypersensitivity to painful stimuli (hyperalgesia), along with abnormal sensations such as burning or stabbing sensations. SNL causes damage to nerve fibers, thereby altering the pattern of neural activity that is interpreted as pain in the brain. The pain caused by SNL can be used as a model for neuropathic pain to study the mechanism of the pain and experimentally confirm new treatment methods and treatments.

Meanwhile, glial cells, which are non-neural cells in the nervous system, are known to be involved in the development and maintenance of neuropathic pain. Particularly within the spinal cord, microglia and astrocytes play an important role in the pathogenesis of neuropathic pain. After nerve injury, microglia and astrocytes become activated and secrete pro-inflammatory cytokines and chemokines that initiate an inflammatory response. This further aggravates inflammation and damage to nerve fibers. Additionally, glial cells also contribute to the development of central sensitization, which is a phenomenon in which nerve cells in the spinal cord become hypersensitive to pain signals. Therefore, treatment methods targeting glial cells within the spinal cord are emerging as a potential alternative for treating neuropathic pain. Since drugs that can inhibit glial cell activation have been shown to alleviate neuropathic pain in SNL animal models, the regulation of glial cells is emerging as a new target for the treatment of neuralgia.

Central sensitization refers to a phenomenon in which pain persists due to changes in the spinal nervous system. c-FOS, which plays an important role in this process, is expressed in response to pain stimulation within the spinal cord. Pain stimuli occurring in the central nervous system are primarily processed in the spinal dorsal horn, and c-FOS expression increases during this processing. As a result, neurons in the central nervous system become sensitive and their response to the same stimulus increases. When this process continues, the central nervous system forms a kind of "memory", which can cause hypersensitivity to stimuli that do not normally cause pain. Therefore, c-FOS protein plays a very important role in understanding and treating pain occurring in the central nervous system. Drugs or techniques that inhibit the expression of c-FOS may have the effect of reducing pain responses in the central nervous system.

PRIOR ART DOCUMENTS

Patent Documents

Korean Patent No. 10-1249930
Korean Patent Application Publication No. 10-1992-0011502

NON-PATENT DOCUMENTS

1. Baron R, et al. (2017) Peripheral neuropathic pain: a mechanism-related organizing principle based on sensory profiles. 158(2):261-272.
2. Finnerup N B, et al. (2015) Pharmacotherapy for neuropathic pain in adults: a systematic review and meta-analysis. 14(2):162-173.
3. Gilron I, Baron R, & Jensen T (2015) Neuropathic pain: principles of diagnosis and treatment. Mayo Clinic Proceedings, (Elsevier), pp 532-545.
4. Jaggi A S, Jain V, Singh NJF, & pharmacology c (2011) Animal models of neuropathic pain. 25(1):1-28.
5. Decosterd I & Woolf CJJP (2000) Spared nerve injury: an animal model of persistent peripheral neuropathic pain. 87(2):149-158.
6. Kim S H & Chung JMJP (1992) An experimental model for peripheral neuropathy produced by segmental spinal nerve ligation in the rat. 50(3):355-363.
7. Devor MJTop (1999) Pathophysiology of damaged nerves in relation to chronic pain. 129-164.
8. Ikeda H, Tsuda M, Inoue K, & Murase KJEJoN (2007) Long-term potentiation of neuronal excitation by neuron-glia interactions in the rat spinal dorsal horn. 25(5):1297-1306.
9. Milligan ED & Watkins LRJNrn (2009) Pathological and protective roles of glia in chronic pain. 10(1):23-36.
10. Ren K & Dubner RJNm (2010) Interactions between the immune and nervous systems in pain. 16(11):1267-1276.
11. Raghavendra V, Tanga F, DeLeo JAJJoP, & Therapeutics E (2003) Inhibition of microglial activation attenuates the development but not existing hypersensitivity in a rat model of neuropathy. 306(2):624-630.
12. Ji R-R, Nackley A, Huh Y, Terrando N, & Maixner WJA (2018) Neuroinflammation and central sensitization in chronic and widespread pain. 129(2):343-366.
13. Gao Y-J & Ji R-RJTopj (2009) c-FOS and pERK, which is a better marker for neuronal activation and central sensitization after noxious stimulation and tissue injury? 2:11.
14. Peirs C, et al. (2021) Mechanical allodynia circuitry in the dorsal horn is defined by the nature of the injury. 109(1):73-90. e77.
15. Malmberg AB & Basbaum AIJP (1998) Partial sciatic nerve injury in the mouse as a model of neuropathic pain: behavioral and neuroanatomical correlates. 76(1-2):215-222.

16. Latremoliere A & Woolf CJJTjop (2009) Central sensitization: a generator of pain hypersensitivity by central neural plasticity. 10(9):895-926.
17. Neumann S, Braz J M, Skinner K, Llewellyn-Smith I J, & Basbaum AIJJoN (2008) Innocuous, not noxious, input activates PKCγ interneurons of the spinal dorsal horn via myelinated afferent fibers. 28(32):7936-7944.

SUMMARY

An object of an embodiment of the present disclosure is to provide a pharmaceutical composition and a pharmacopuncture composition for treating or preventing neuropathic pain.

An object of an embodiment of the present disclosure is to provide a pharmaceutical composition and a pharmacopuncture composition which have an excellent anti-inflammatory effect.

In addition to the objects above, other embodiments according to the present disclosure may also be used to achieve other objects that are not specifically mentioned.

A pharmaceutical composition for treating or preventing neuropathic pain according to an embodiment includes *Polygonati rhizoma, Sorbus commixta* Hedl., *Geranium nepalense*, and *Glycine Semen Preparata*.

Mixed herbal medicine may further include *Imperata cylindrica*.

The pharmaceutical composition may be a formulation of a preparation for oral administration.

A pharmaceutical drug for preventing or treating neuropathic pain according to an embodiment of the present disclosure includes the pharmaceutical composition.

A pharmacopuncture composition for treating or preventing neuropathic pain according to an embodiment of the present disclosure includes the pharmaceutical composition.

The concentration of the pharmacopuncture composition is 0.015 g/mL to 0.03 g/mL.

A method for preparing a pharmacopuncture composition for treating or preventing neuropathic pain according to an embodiment of the present disclosure includes curing a mixture of mixed herbal medicine, which includes *Polygonati rhizoma, Sorbus commixta* Hedl., *Geranium nepalense*, and *Glycine Semen Preparata*, and ultrapure liquid at 65° C. to 80° C. for 48 to 60 hours; heating the cured mixture to obtain an extract; distilling the extract to obtain a distilled extract, and mixing the distilled extract with ultrapure liquid and then adjusting the salinity and acidity (pH) of the mixture.

The mixed herbal medicine may further include *Imperata cylindrica*.

DETAILED DESCRIPTION

Figure 1A:
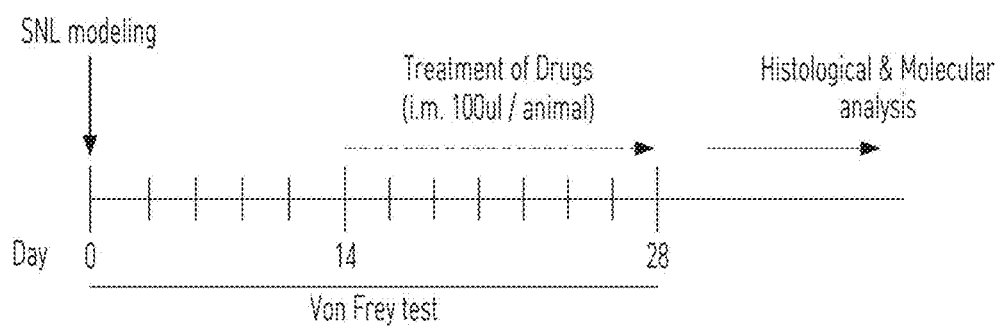
FIG. 1A is a diagram showing the experimental sequence and procedure for the effects of pharmaceutical compositions and pharmacopuncture compositions according to embodiments.

With reference to the accompanying drawings, the embodiments of the present disclosure are described in detail so that those with ordinary knowledge in the technical field to which the present disclosure belongs can easily practice the same. The present disclosure can be implemented in many different forms and is not limited to the embodiments described herein. In order to clearly describe the present disclosure in the drawings, parts not related to the description are omitted, and the same reference numerals are used for identical or similar components throughout the specification. Additionally, in the case of widely-known well-known technologies, detailed descriptions thereof are omitted.

Throughout the specification, when a part is described to "include" a certain component, this means that it may further include other elements rather than excluding other elements, unless specifically stated to the contrary.

Throughout the specification, the term "composition" refers to a material in which two or more components are uniformly mixed, and is a concept that includes not only finished products but also intermediate materials for preparing finished products.

The present disclosure relates to a novel pharmaceutical composition and a novel pharmacopuncture composition (Entrapment Neuropathy Unties, ENU), which have an excellent effect on prevention, improvement, and treatment of neuropathic pain.

In addition, the pharmaceutical compositions according to embodiments may have an excellent effect on prevention, improvement, and treatment of inflammation, and may be harmless to the human body and have excellent safety because they are based on natural medicinal materials.

The pharmaceutical compositions according to embodiments include an extract of mixed herbal medicine including *Polygonati rhizoma, Sorbus commixta* Hedl., *Geranium nepalense*, and *Glycine Semen Preparata* as an active ingredient.

The pharmaceutical compositions may alleviate mechanical allodynia.

Meanwhile, since c-FOS protein is an immediate early gene and reflects neural activity, and pain stimulation occurring in the central nervous system increases the expression of c-FOS protein in the spinal dorsal horn, c-FOS protein may play an important role in alleviating and treating pain occurring in the central nervous system. The pharmaceutical compositions according to an embodiment may inhibit the expression of such c-FOS protein.

In addition, these pharmaceutical compositions may exhibit an anti-inflammatory effect.

Due to these effects, the pharmaceutical compositions according to the embodiments may exhibit improvement and treatment effects on pain by restoring the function of spinal nerves.

Conventionally, the fruits of *Sorbus commixta* Hedl. and *Polygonati rhizoma* is known to have an effect on inhibiting neuralgia, but *Geranium nepalense* and *Glycine Semen Preparata* have not been disclosed or taught in relation to their effects on alleviating neuropathic pain.

The composition of the mixed herbal medicine including *Polygonati rhizoma, Sorbus commixta* Hedl., *Geranium nepalense*, and *Glycine Semen Preparata* is a new combination not disclosed in the prior art, and the pharmaceutical composition including the herbal medicine extract of such composition also corresponds to a novel composition not disclosed in the prior art.

When the mixed herbal medicine includes *Polygonati rhizoma, Sorbus commixta* Hedl., *Geranium nepalense*, and *Glycine Semen Preparata*, the effects for prevention, improvement, and treatment of neuropathic pain are shown to be more excellent due to the synergistic effect.

Based on the total weight of the mixed herbal medicine, the weight ratio of *Polygonati rhizoma, Sorbus commixta* Hedl., *Geranium nepalense*, and *Glycine Semen Preparata* may be about 1:1:1:1, and at this weight ratio, the effects for prevention, improvement, and treatment of neuropathic pain may be further enhanced.

The mixed herbal medicine in the pharmaceutical composition may further include *Imperata cylindrica*. *Imperata cylindrica* corresponds to a material whose efficacy in alleviating neuropathic pain is not known at all.

In the case of the pharmaceutical compositions according to embodiments, an *Imperata cylindrica* extract, by generating an additional synergistic effect, can further improve the effects of alleviating and improving neuropathic pain and further improve the anti-inflammatory effect.

In addition, the composition of the mixed herbal medicine including *Polygonati rhizoma, Sorbus commixta* Hedl., *Geranium nepalense, Glycine Semen Preparata*, and *Imperata cylindrica* corresponds to a new combination different from the prior art, and the pharmaceutical composition including the herbal medicine extract of such composition also corresponds to a novel composition.

When the mixed herbal medicine includes all of *Polygonati rhizoma, Sorbus commixta* Hedl., *Geranium nepalense, Glycine Semen Preparata*, and *Imperata cylindrica*, the effects for prevention, improvement, and treatment of neuropathic pain may be shown to be more excellent due to the synergistic effect. Additionally, when the mixed herbal medicine includes all of *Polygonati rhizoma, Sorbus commixta* Hedl., *Geranium nepalense, Glycine Semen Preparata*, and *Imperata cylindrica*, the effects of improving and treating pain may be exhibited to be more excellent even compared to the case when the mixed herbal medicine includes all of *Polygonati rhizoma, Sorbus commixta* Hedl., *Geranium nepalense*, and *Glycine Semen Preparata*.

Based on the total weight of the mixed herbal medicine, the weight ratio of *Polygonati rhizoma, Sorbus commixta* Hedl., *Geranium nepalense, Glycine Semen Preparata*, and *Imperata cylindrica* may be about 1:1:1:1, and at this weight ratio, the effects for prevention, improvement, and treatment of neuropathic pain may be further enhanced.

Since the pharmaceutical composition includes, as an active ingredient, an extract of mixed herbal medicine that have little toxicity or side effects, the pharmaceutical composition may be safely used even when administered for a long period of time for preventive purposes.

Meanwhile, the pharmaceutical composition may include pharmaceutically active ingredients other than the above-mentioned ingredients, or may be mixed with a pharmaceutical composition including other active ingredients.

The pharmaceutical compositions according to embodiments may be used as a pharmaceutical drug for treating or preventing neuropathic pain.

The pharmaceutical composition may be a formulation of a preparation for oral administration. In particular, solid preparations for oral administration may be in the form of powders, granules, tablets, capsules, soft capsules, pills, etc. Additionally, liquid preparations for oral administration may be in the form of suspensions, liquid preparations for internal use, emulsions, syrups, gels, aerosols, etc. The preferred dose of the composition varies depending on the degree of absorption, inactivation rate and excretion rate of active ingredients in the body, age, sex, and condition of the patient, and severity of the disease to be treated, but can be appropriately selected by those skilled in the art.

The pharmaceutical compositions according to embodiments may further include commonly used excipients, disintegrants, sweeteners, lubricants, flavoring agents, etc. For example, as excipients, materials such as lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, and polyvinyl pyrrolidone, may be used. As disintegrants, for example, sodium starch glycolate, crospovidone, alginic acid, carboxymethyl cellulose calcium, carboxymethyl cellulose sodium, chitosan, guar gum, low-substituted hydroxypropyl cellulose, magnesium aluminum silicate, etc. may be used.

The pharmaceutical composition may further include a pharmaceutically acceptable additive. In particular, the pharmaceutically acceptable additive may include, for example, starch, gelatinized starch, microcrystalline cellulose, lactose, povidone, colloidal silicon dioxide, calcium hydrogen phosphate, lactose, mannitol, arabic gum, hydroxypropyl cellulose, sodium starch glycolate, carbauba wax, stearic acid, magnesium stearate, aluminum stearate, calcium stearate, white sugar, taffy, dextrose, sorbitol, talc, etc., but is not limited thereto. The pharmaceutically acceptable additive may be included in an amount of about 0.1 parts by weight to about 90 parts by weight based on the entire pharmaceutical composition.

The pharmaceutical compositions may be prepared by further including one or more pharmaceutically acceptable carriers for administration. In particular, as the pharmaceutically acceptable carrier, a saline solution, sterile water, Ringer's solution, buffered saline solution, dextrose solution, maltodextrin solution, glycerol, ethanol, and a mixture of one or more of these components may be used.

The pharmacopuncture compositions for treating or preventing neuropathic pain according to embodiments may include a pharmaceutical composition, which includes an extract of mixed herbal medicine including *Polygonati rhi*- zoma, *Sorbus commixta* Hedl., *Geranium nepalense*, and *Glycine Semen Preparata* as active ingredients.

The pharmacopuncture composition is administered directly through the skin and may alleviate or treat neuropathic pain more quickly and effectively than formulations for oral administration.

In particular, the concentration of the pharmacopuncture composition may be about 0.015 g/mL to about 0.03 g/mL. Within this concentration range, the effect of neuropathic pain alleviation may be maximized.

The pharmacopuncture compositions for treating or preventing neuropathic pain according to embodiments may include a pharmaceutical composition, which includes an extract of mixed herbal medicine including *Polygonati rhizoma*, *Sorbus commixta* Hedl., *Geranium nepalense*, *Glycine Semen Preparata*, and *Imperata cylindrical* as active ingredients. The concentration of the pharmacopuncture composition may be about 0.015 g/mL to about 0.03 g/mL. Within this concentration range, the effect of alleviating neuropathic pain may be maximized.

The pharmacopuncture composition may be prepared through the following steps.

First, mixed herbal medicine is washed and dried, then mixed with ultrapure liquid, and cured in a concentrator at a low temperature.

In particular, low-temperature curing may be performed at about 65° C. to about 80° C. for about 48 hours to about 60 hours. When low-temperature curing is performed within this temperature and time range, the bonds between cells are broken and the herbal medicine becomes to have a low molecular weight due to curing, thus making it possible to extract active ingredients during extraction. In addition, through low-temperature curing, the starch present in the herbal medicine is enzymatically decomposed, which increases the sugar content, improves the taste and the aroma, increases the absorption rate into the body, and generates more antioxidant enzymes, thereby helping to improve skin, prevent curing, and purify body waste. When curing is performed at 80° C. or above, the active ingredients of herbal medicine may be destroyed.

After the low-temperature curing process, the obtaining of an extract after heating is performed.

In particular, heating is performed at about 105° C. to about 115° C. for about 1 to 3 hours, and in this temperature and time range, an extract without denaturation or deterioration of the active ingredients may be obtained, and the concentration of the extract may be increased.

Then, the obtaining of a distilled extract is performed.

The distilled extract may be obtained by distilling the extract obtained in the previous step at about 105° C. to about 120° C. through a distiller, and in this temperature range, a distilled extract without denaturation or deterioration of the active ingredients can be obtained.

Then, the preparing of a mixture of herbal medicine by mixing the distilled extract with an ultrapure liquid, and of the adjusting of the salinity and acidity (pH) of the mixture of herbal medicine are performed.

Salinity may be adjusted to about 0.75% to about 0.98%, and pH may be adjusted to a range of about 7.25 to about 7.85. Within this range, the pharmacopuncture mixture may be adjusted to a level similar to the salinity of body fluids, and the pH may be adjusted to be slightly acidic, thereby facilitating absorption into tissues.

Then, the obtaining of a pharmacopuncture composition through a two-step filtration step is performed.

The first filtration step may be performed with a membrane filter with an average pore size of about 0.4 µm to about 0.5 µm, and the second filtration step may be performed with a membrane filter with an average pore size of about 0.05 µm to about 0.15 µm.

The obtained pharmacopuncture composition may be stored by going through a stabilization step after stirring.

Hereinafter, the present disclosure will be described in more detail, including Examples and Experimental Examples, but the present disclosure is not limited to these examples.

Example 1—Pharmacopuncture Composition

A mixed herbal medicine, which includes 100 g of *Polygonati rhizoma*, 100 g of *Sorbus commixta* Hedl., 100 g of *Geranium nepalense*, 100 g of *Glycine Semen Preparata*, and 100 g of *Imperata cylindrica*, was prepared and washed with running water.

After washing, the moisture was removed, and then 500 g of herbal medicine and 5,000 g of ultrapure liquid were added together into an extraction concentrator (extraction, concentration, and distillation; Daehan Median Co., Ltd.) and the mixture was subjected to low-temperature curing at 72° C. for 54 hours.

Then, the resultant was heated at 110° C. for 2 hours, and the pressure valve was opened at the time point when the pressure gauge reached 0.15 MPa to remove the herbal medicine flavor generated by heating, and thereby 4,300 g of an extract was obtained.

Then, 4,300 g of the extract was distilled at 112° C. using a distiller (Daehan Median Extractor) to obtain 4,000 g of a distilled extract.

Then, a pharmacopuncture mixture was prepared by mixing the distilled extract with ultrapure liquid, and the salinity was adjusted to 0.87% and pH was adjusted to 7.55.

Then, the pharmacopuncture mixture with adjusted salinity and pH was first filtered through a membrane with an average pore size of 0.45 µm, and secondly filtered through a membrane with an average pore size of 0.1 µm, and thereby a pharmacopuncture composition was obtained.

Subsequently, the filtered composition was stirred in a bioclean room at 500 rpm for 1 hour using a stirrer and allowed to stabilize for 1 hour, and the pharmacopuncture composition was aliquoted into sterilized vials using an auto dispenser, capped with sterilized silicone stoppers and aluminum caps, and stored after autoclave sterilization at 127° C. for about 27 minutes.

The total volume of the pharmacopuncture composition contained in one vial bottle was 10 cc (10 mL), the weight of the distilled extract contained in each vial bottle was 0.075 g, and thus, the concentration of the pharmacopuncture composition was 0.0075 g/mL.

Example 2—Pharmacopuncture Composition

The pharmacopuncture composition was prepared in the same manner as in Example 1, except that the total volume of a pharmacopuncture composition contained in one vial bottle was 10 cc (10 mL), the weight of a distilled extract contained in each vial bottle was 0.15 g, and thus, the concentration of the pharmacopuncture composition was 0.015 g/mL.

Example 3—Pharmacopuncture Composition

The pharmacopuncture composition was prepared in the same manner as in Example 1, except that the total volume of a pharmacopuncture composition contained in one vial bottle was 10 cc (10 mL), the weight of a distilled extract contained in each vial bottle was 0.3 g, and thus, the concentration of the pharmacopuncture composition was 0.03 g/mL.

Example 4—Composition for Oral Administration

A mixed herbal medicine, which includes 4 g of *Polygonati rhizoma*, 4 g of *Sorbus commixta* Hedl., 4 g of *Geranium nepalense*, 4 g of *Glycine Semen Preparata*, and 4 g of *Imperata cylindrica*, was prepared and washed with running water.

After washing, the moisture was removed, then 20 g of herbal medicine and 200 g (200 cc) of ultrapure liquid were mixed, and the mixture was subjected to hot water extraction curing for about 2 hours, and thereby 100 g of a distilled extract (pharmaceutical composition for oral administration) was obtained.

Example 5—Pharmacopuncture Composition

A mixed herbal medicine, which includes 100 g of *Polygonati rhizoma*, 100 g of *Sorbus commixta* Hedl., 100 g of *Geranium nepalense*, and 100 g of *Glycine Semen Preparata*, was prepared and washed with running water.

After washing, the moisture was removed, and then 540 g of herbal medicine and 4,000 g of ultrapure liquid were added together into an extraction concentrator (extraction, concentration, and distillation; Daehan Median Co., Ltd.) and the mixture was subjected to low-temperature curing at 72° C. for 54 hours.

Then, the resultant was heated at 110° C. for 2 hours, and the pressure valve was opened at the time point when the pressure gauge reached 0.15 MPa to remove the herbal medicine flavor generated by heating, and thereby 3,440 g of an extract was obtained.

Then, 3,440 g of the extract was distilled at 112° C. using a distiller (Daehan Median Extractor) to obtain 3,200 g of a distilled extract.

Then, a pharmacopuncture mixture was prepared by mixing the distilled extract with ultrapure liquid, and the salinity was adjusted to 0.87% and pH was adjusted to 7.55.

Then, the pharmacopuncture mixture with adjusted salinity and pH was first filtered through a membrane with an average pore size of 0.45 μm, and secondly filtered through a membrane with an average pore size of 0.1 μm and thereby a pharmacopuncture composition was obtained.

Subsequently, the filtered composition was stirred in a bioclean room at 500 rpm for 1 hour using a stirrer and allowed to stabilize for 1 hour, and the pharmacopuncture composition was aliquoted into sterilized vials using an auto dispenser, capped with sterilized silicone stoppers and aluminum caps, and stored after autoclave sterilization at 127° C. for about 27 minutes.

The total volume of the pharmacopuncture composition contained in one vial bottle was 10 cc (10 mL), the weight of the distilled extract contained in each vial bottle was 0.15 g, and thus, the concentration of the pharmacopuncture composition was 0.015 g/mL.

Comparative Example 1

A mixed herbal medicine, which includes 100 g of *Polygonati rhizoma*, 100 g of *Sorbus commixta* Hedl., and 100 g of *Geranium nepalense*, was prepared and washed with running water.

After washing, the moisture was removed, and then 300 g of herbal medicine and 3,000 g of ultrapure liquid were added together into the Extraction Concentrator (extraction, concentration, and distillation; Daehan Median Co., Ltd.) and the mixture was subjected to low-temperature curing at 72° C. for 54 hours.

Then, the resultant was heated at 110° C. for 2 hours, and the pressure valve was opened at the time point when the pressure gauge reached 0.15 MPa to remove the herbal medicine flavor generated by heating, and thereby 2,580 g of an extract was obtained.

Then, 2,580 g of the extract was distilled at 112° C. using a distiller (Daehan Median Extractor) to obtain 2,400 g of a distilled extract.

Then, a pharmacopuncture mixture was prepared by mixing the distilled extract with ultrapure liquid, and the salinity was adjusted to 0.87% and pH was adjusted to 7.55.

Then, the pharmacopuncture mixture with adjusted salinity and pH was first filtered through a membrane with an average pore size of 0.45 μm, and secondly filtered through a membrane with an average pore size of 0.1 μm to thereby obtain a pharmacopuncture composition.

Subsequently, the filtered composition was stirred in a bioclean room at 500 rpm for 1 hour using a stirrer and allowed to stabilize for 1 hour, and the pharmacopuncture composition was aliquoted into sterilized vials using an auto dispenser, capped with sterilized silicone stoppers and aluminum caps, and stored after autoclave sterilization at 127° C. for 27 minutes.

The total volume of the pharmacopuncture composition contained in one vial bottle was 10 cc (10 mL), the weight of the distilled extract contained in each vial bottle was 0.15 g, and thus, the concentration of the pharmacopuncture composition was 0.015 g/mL.

For experiments on the compositions according to Examples 1 to 5 and Comparative Example, a neuropathic pain animal model was prepared, groups were divided, and pharmacopuncture treatment or oral administration of the composition was performed.

The herbal medicine used in the following experiments was standard herbal medicine purchased from Nami Pharmaceutical Co., Ltd. (Yeongcheon-si, Gyeongsangbuk-do).

The experimental animals used in the following experiments were 6-week-old ICR male mice (20 g to 25 g) supplied by DBL Co., Ltd. (Eumseong-gun, Chungcheongbuk-do, Korea), acclimatized for one week, and then used to prepare animal models. During the experiment period, the animals were *ad libitum* fed with a certain amount of solid feed and purified water, and the day/night cycle was 12 hours (day light: 08:00 to 20:00), and constant breeding conditions were maintained until the end of the experiment by maintaining a room temperature of about 23±2° C. and humidity of about 50±10%.

To specifically describe the immunofluorescence staining method used in the following experiments, each mouse was anesthetized with Avertin (50 mg/kg, i.p.) and the heart was perfused with 50 mL of phosphate buffered saline (PBS) followed by 80 mL of a 4% formalin solution prepared in phosphate buffer. Upon completion of fixation of each mouse, the spinal cord and dorsal root ganglia (DRG) were taken out, post-fixed for 24 hours with the same fixative, and stored in PBS containing 30% sucrose at 4° C. for one day. On the next day, the tissue was quickly frozen and cut into 8-10 μm pieces. The sectioned tissues were washed 3 times for 10 minutes with Tris buffer solution (TBST) containing 0.3% triton-X100, and reacted for 1 hour with a solution of 5% bovine serum albumin (BSA) diluted in TBST. Primary antibodies to c-FOS (1:2000, rabbit monoclonal, Immun-Smol) and GFAP (1:1000, guinea pig monoclonal, Abcam) were prepared by diluting in TBST containing 5% BSA. Tissues were reacted with primary antibodies at 4° C. for 24 hours. Then, the brain tissue was washed with TBST and then reacted with secondary antibodies at room temperature for 2 hours. Secondary antibodies to Alexa anti-rabbit 488 (1:2000, Invitrogen), Alexa anti-mouse 594 (1:2000, Invitrogen), or Alexa anti-guinea pig 594 (1:2000, Invitrogen) were prepared by diluting in TBST containing 5% BSA. After rinsing 3 times with TBST, the secondary antibodies were sealed in polymount. The expression level in each part of the tissue was observed and photographed using a confocal microscope.

Quantitative real-time PCR (qPCR) for measuring mRNA levels below was performed with an ABI PRISM 7700 Sequence Detection System Instrument and software (Applied Biosystems, Foster City, CA, USA) using the manufacturer's recommended conditions. Total RNA was isolated from the footpad tissue of ICR mice (TRIzol reagent, Invitrogen, CA), and cDNA was synthesized through reverse transcription (Superscript III, Invitrogen, CA). Quantitative PCR analysis was performed using SYBER Green Master Mix (Invitrogen, CA). Amplification coefficients were calculated using the comparative threshold cycle (Ct) method, and primer sequences were identified, and the relative amount of a target was normalized to the level of glyceraldehyde 3-phosphate dehydrogenase (GAPDH).

All experimental results were expressed as the mean and standard deviation (mean±SE) of at least 3 repeated experiments, and statistical significance was tested using two-way ANOVA (Bonferroni post hoc multiple comparison test) and one-way ANOVA (Tukey's test) using the GraphPad Prism 8.0 analysis program (GraphPad Software, CA, USA).

Preparation of Neuropathic Pain Animal Model—SNL Model

After anesthetizing each mouse with 2.0% isoflurane, the skin on the back of the left hip joint was shaved and incised, and the sciatic nerve between the biceps femoris muscles was located and separated from the surrounding tissues and blood vessels using a microforcep. Then, the sciatic nerve was ligated twice with 4.0 silk thread. Kanamycin was instilled into the incised area and the skin was sutured.

Separation of Groups

A total of 42 white mice were divided into normal (n=6), a control group in which saline was administered to the affected area after SNL modeling (Control (saline injection), n=6), a control group in which saline was orally administered after SNL modeling (Control (oral), n=6), a treatment group in which the pharmacopuncture composition according to Comparative Example 1 was administered to the affected area after SNL modeling (Comparative Example 1, n=6), a treatment group in which the pharmacopuncture composition according to Example 1 was administered to the affected area after SNL modeling (Example 1, n=6), a treatment group in which the pharmacopuncture composition according to Example 2 was administered to the affected area after SNL modeling (Example 2, n=6), a treatment group in which the pharmacopuncture composition according to Example 3 was administered to the affected area after SNL modeling (Example 3, n=6), a treatment group in which the pharmacopuncture composition according to Example 5 was administered to the affected area after SNL modeling (Example 5, n=6), and a treatment group in which the composition for oral administration according to Example 4 was orally administered after SNL modeling (Example 4, n=6).

Pharmacopuncture Treatment

The pharmacopuncture treatment of the pharmacopuncture compositions according to Example 1, Example 2, Example 3, Example 5, and Comparative Example 1 was performed using an insulin syringe (31 G×8 mm, BD, USA) from day 14 after the induction of neuropathic pain to the day 28, by administering 100 μL of the pharmacopuncture composition to the affected area around the ligated sciatic nerve for a total of 7 times, once every 2 days. The Normal group and the Control group were administered with the same amount of a saline solution.

Oral Administration

The composition for oral administration according to Example 4 was orally administered at a dose of 1 mL/time, and the Control group was administered with the same amount of a saline solution.

Experimental Example 1—Measurement of Mechanical Allodynia

Figure 1B:
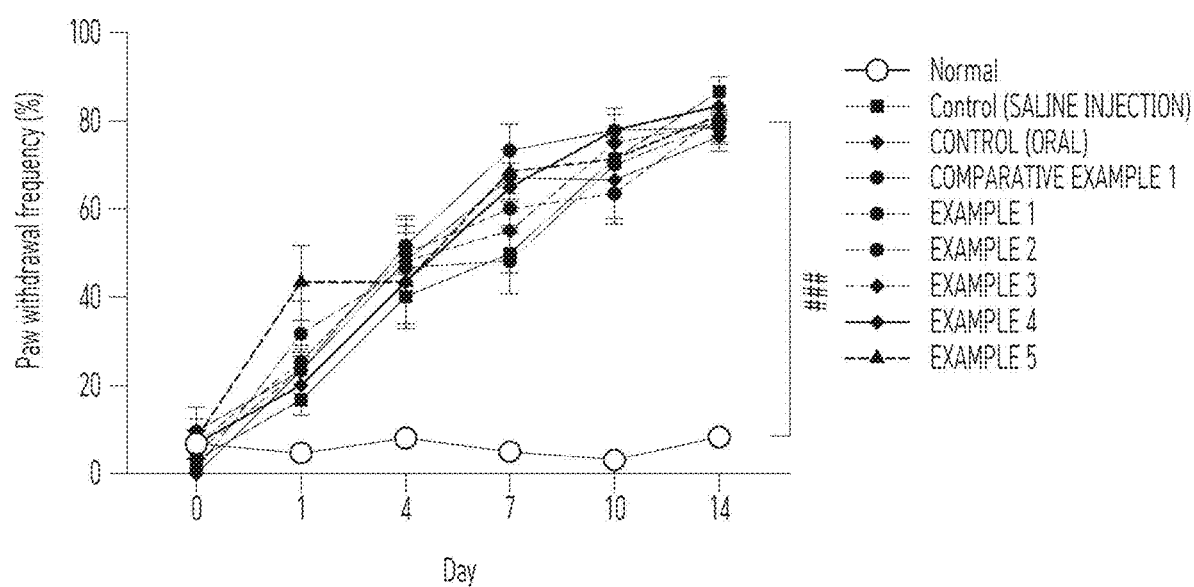
FIG. 1B is a graph showing the increase in mechanical allodynia over 14 days after pain induction.

In order to induce a neuropathic animal model, the left sciatic nerve was ligated to induce neuropathic pain, and then the Von Frey test was performed on day 1, day 3, day 7, day 10, and day 14 for 14 days (see FIG. 1A). During the same period (14 days), mechanical allodynia was statistically significantly increased in all groups compared to the Normal group (see FIG. 1B, p<0.001).

In order to describe the experimental method in detail, the frequency of avoidance responses induced in the soles of the feet was measured after applying physical stimulation to the soles of the mice using Von frey filament (Touch test 3.61 (0.4 g), North Coast Medical Inc., UK). In order to measure the avoidance response in the paw, each white mouse was placed in a transparent acrylic container (10 cm×10 cm×10 cm) and was given about 30 minutes of time to adapt to the environment, and the presence/absence of compliance was confirmed, and the soles of the feet were stimulated with quantified Von Frey filaments between the wire mesh grids. In the case where the avoidance response after a total of 10 stimulations (frequency of 1 time per 10 seconds) of each hind paw was to the extent that the Von Frey filaments were slightly bent, the response was considered as a positive response.

After the administration of the compositions according to Examples 1 to 5 and Comparative Example 1, examinations were conducted in relation to acute analgesic efficacy through single administration of the composition, and mechanical allodynia for 1, 3, 7, 12, 24, 32, and 48 hours after single administration so as to set up a repeat administration period (an experiment on acute analgesic effect), and based on the effect of one-time administration, mechanical allodynia was tested a total of 7 times, once every 2 days from day 14 to day 28 after the induction of neuropathic pain (an experiment on analgesic effect).

Figure 2A:
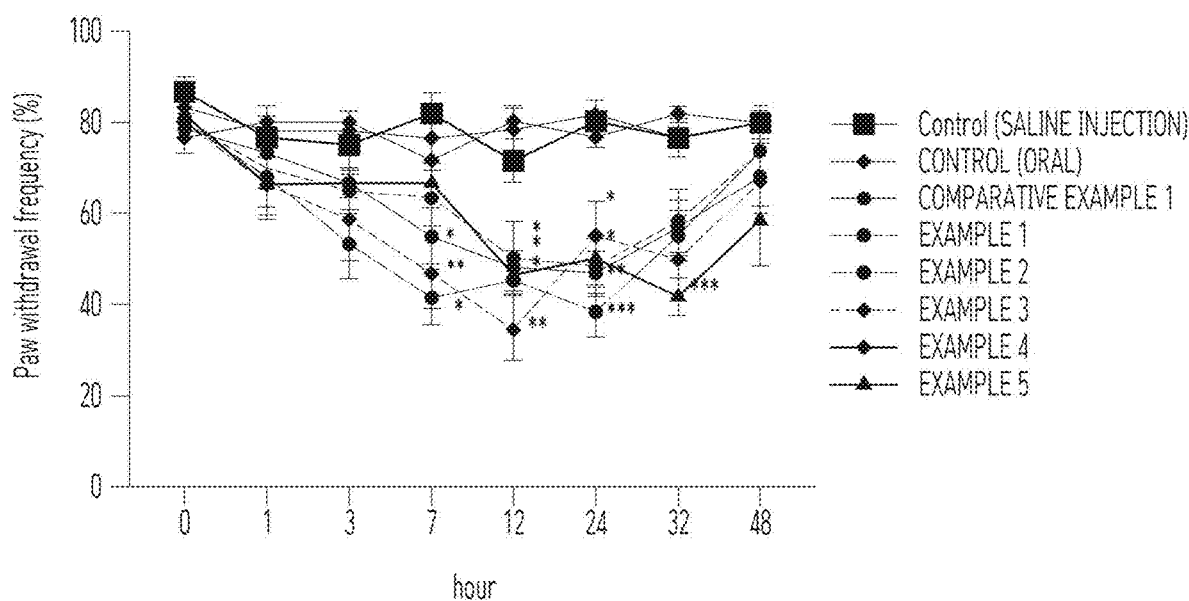
FIG. 2A is a graph showing the results of an acute analgesic test (paw withdrawal frequency) for 48 hours after administration of a composition.
Figure 2B:
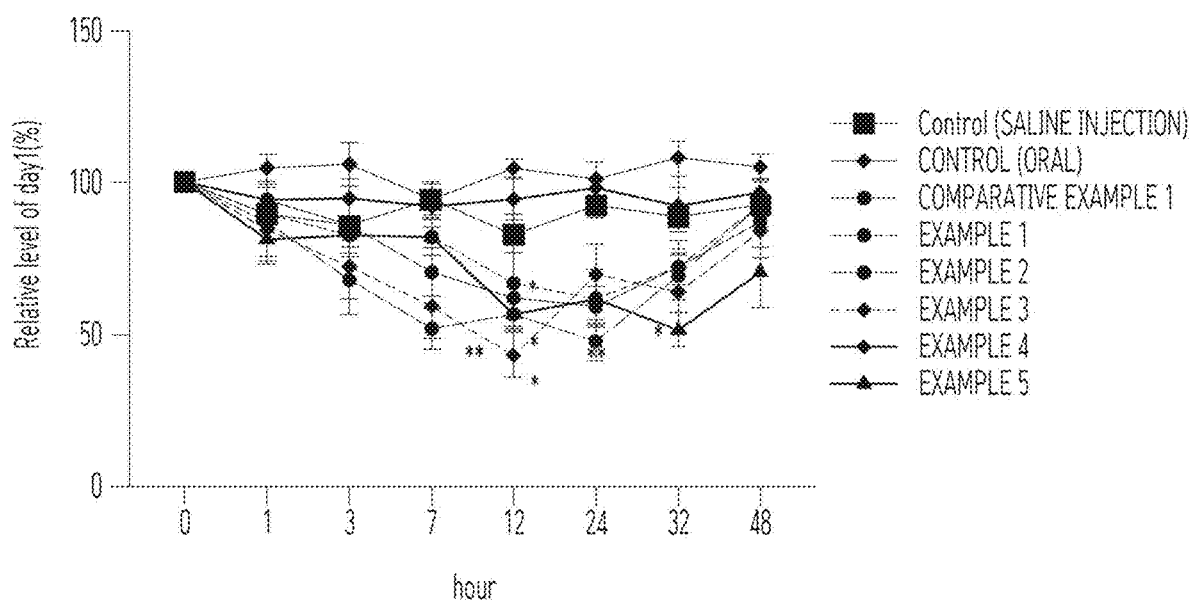
FIG. 2B is a graph illustrating the relative acute analgesic effect based on 0 h.

Regarding the acute analgesic effect, FIG. 2A shows a graph illustrating the results of an acute analgesic experiment (Paw withdrawal frequency) for 48 hours after administration of the composition, and FIG. 2B shows a graph illustrating the relative acute analgesic effect based on the time point of 0 hour.

The results were expressed in the form of mean±standard deviation (Mean±SEM). In the graphs, * indicates a case where statistical significance p is less than 0.05,  indicates a case where statistical significance p is less than 0.01, and * indicates a case where statistical significance p is less than 0.001. In the description of the graphs below, as for the parts relating to the result display format and statistical significance, the same descriptions are omitted.

In order to confirm the acute analgesic effect, the effect of reducing mechanical allodynia was measured using Von Frey filaments.

Referring to FIGS. 2A and 2B, the administration of the composition of Comparative Example 1 to neuropathy-induced mice showed a reduction in pain compared to the Control group (saline injection) and other groups at the time points of 7, 12, and 24 hours ($p<0.05$, $p<0.01$). The administration of the composition of the Example 1 showed a tendency to reduce pain, and the compositions of Example 2 and Example 3 showed a more significant analgesic effect compared to the Control group (saline injection) and other groups at the time points of 7, 12, and 24 hours ($p<0.05$, $p<0.01$), $p<0.001$). The administration of the composition of Example 5 showed a superior reduction in pain compared to the Control group (saline injection) and other groups at the time points of 12, 24, and 32 hours ($p<0.05$, $p<0.001$).

Figure 3A:
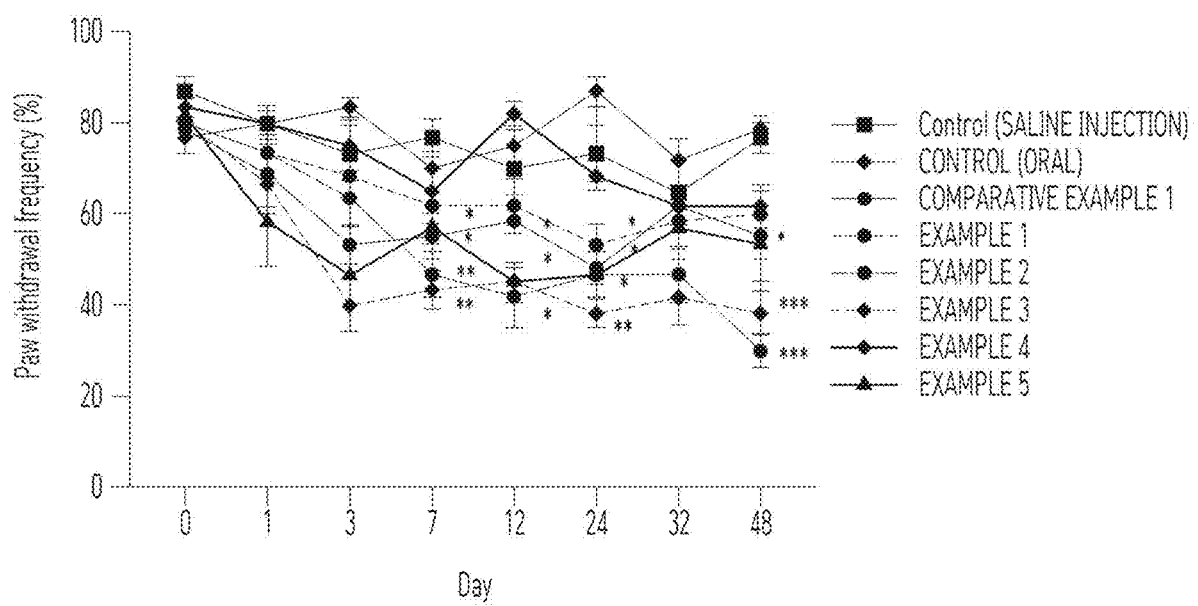
FIG. 3A is a graph showing the results of an analgesic test by examining mechanical allodynia a total of 7 times, once every two days, from day 14 to day 28 after pain induction.
Figure 3B:
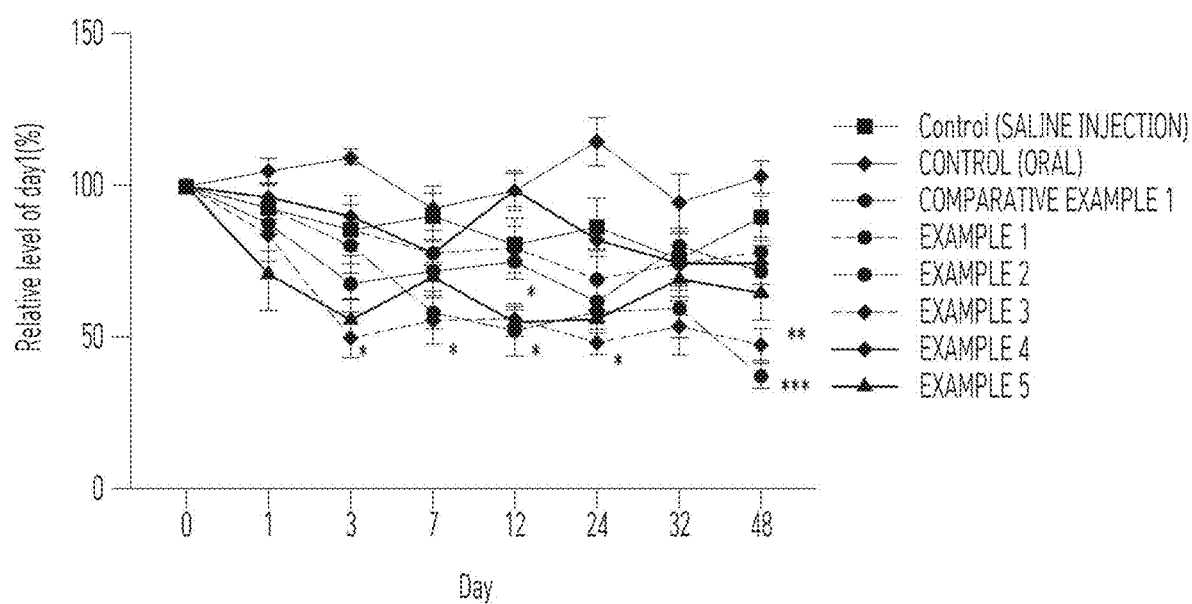
FIG. 3B is a graph showing the relative analgesic effect based on day 0.

Regarding the analgesic effect, FIG. 3A shows a graph illustrating the results of the analgesic experiment by examining mechanical allodynia a total of 7 times, once every 2 days, from day 14 to day 28 after pain induction, and FIG. 3B shows a graph illustrating the relative analgesic effect based on the time point of 0 day.

In order to confirm the analgesic effect, the effect of reducing mechanical allodynia was measured using Von Frey filaments.

Referring to FIGS. 3A and 3B, the administration of the composition of Comparative Example 1 to mice induced with neuropathic pain showed a decrease in pain compared to the Control group (saline injection) at the time points on day 6, day 8, day 10, and day 14 ($p<0.05$). The administration of the composition of Example 2 showed a reduction in pain compared to Control (saline injection) and other groups at the time points on day 6, day 8, day 10, and day 14, and showed the best effect on day 14, which is the last day ($p<0.05$, $p<0.01$, $p<0.001$). The administration of the composition of Example 3 showed an analgesic effect starting on day 4 ($p<0.05$), and showed a significant analgesic effect compared to the Control (saline injection) and other groups administered physiological saline on day 6, day 8, day 10, and day 14 ($p<0.05$, $p<0.01$, $p<0.001$). In the case of compositions of Examples 2 and 3, it can be seen that the analgesic effect was higher by more than 50% compared to before administration. The administration of the composition of Example 5 showed a significant reduction in pain on day 4, day 8, and day 10 ($p<0.05$).

Experimental Example 2—Experiment on Inhibition of C-FOS Expression

In order to confirm the abnormal activity of neurons within the spinal nerve due to SNL, the expression of C-FOS was confirmed through immunohistochemical staining in the spinal dorsal horn ipsilateral to the damaged sciatic nerve.

Figure 4A:
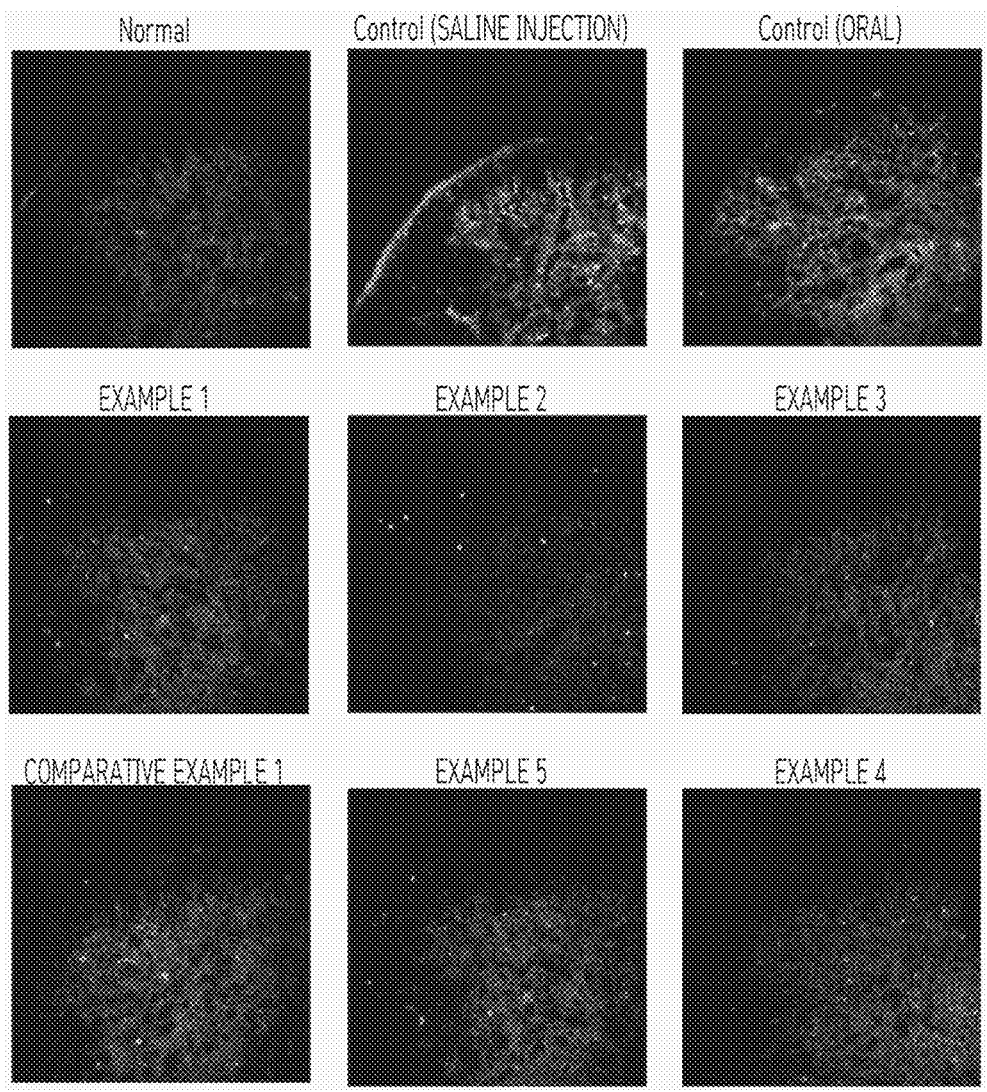
FIG. 4A are images showing the effect of inhibiting C-FOS protein expression in spinal nerves by repeated administration of the composition according to Examples 1 to 5 and Comparative Example 1.
Figure 4B:
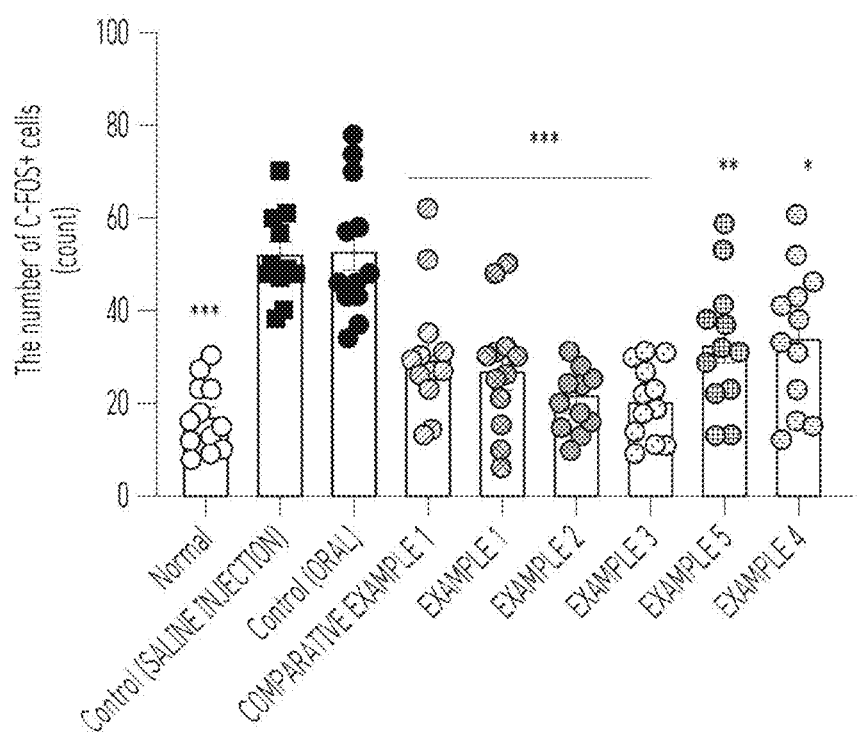
FIG. 4B is a graph showing the number of C-FOS positive cells counted.

FIG. 4A images showing the effect of inhibiting C-FOS protein expression in spinal nerves by repeated administration of the composition according to Examples 1 to 5 and Comparative Example 1, and FIG. 4B is a graph showing the number of C-FOS positive cells counted.

Referring to FIGS. 4A and 4B, SNL significantly increased the expression of C-FOS in the spinal dorsal horn compared to the Normal group (vs. the Control group (saline injection) or the Control group (oral), $p<0.001$). The administration of the composition of Comparative Example 1 showed a statistically significant decrease in C-FOS expression compared to the Control group (saline injection) ($p<0.001$). The administration of the compositions of Examples 1, 2, and 3 significantly reduced the expression of C-FOS compared to the Control group (saline injection) ($p<0.001$), and it was confirmed that the expression of C-FOS was reduced in a concentration-dependent manner. The administration of the composition of Example 5 statistically significantly reduced the expression of C-FOS compared to the Control group (saline injection) ($p<0.01$). The administration of the composition of Example 4 also significantly reduced the expression of C-FOS compared to the Control group (oral) ($p<0.05$).

Experimental Example 3—Experiment on Inhibition of GFAP Expression

In order to confirm the activity of inflammatory cells in the spinal nerves due to SNL, the expression of the astrocytes (inflammatory cells) marker GFAP was confirmed through immunofluorescence staining in tissue sections of the ipsilateral spinal dorsal horn of the damaged sciatic nerve.

Figure 5A:
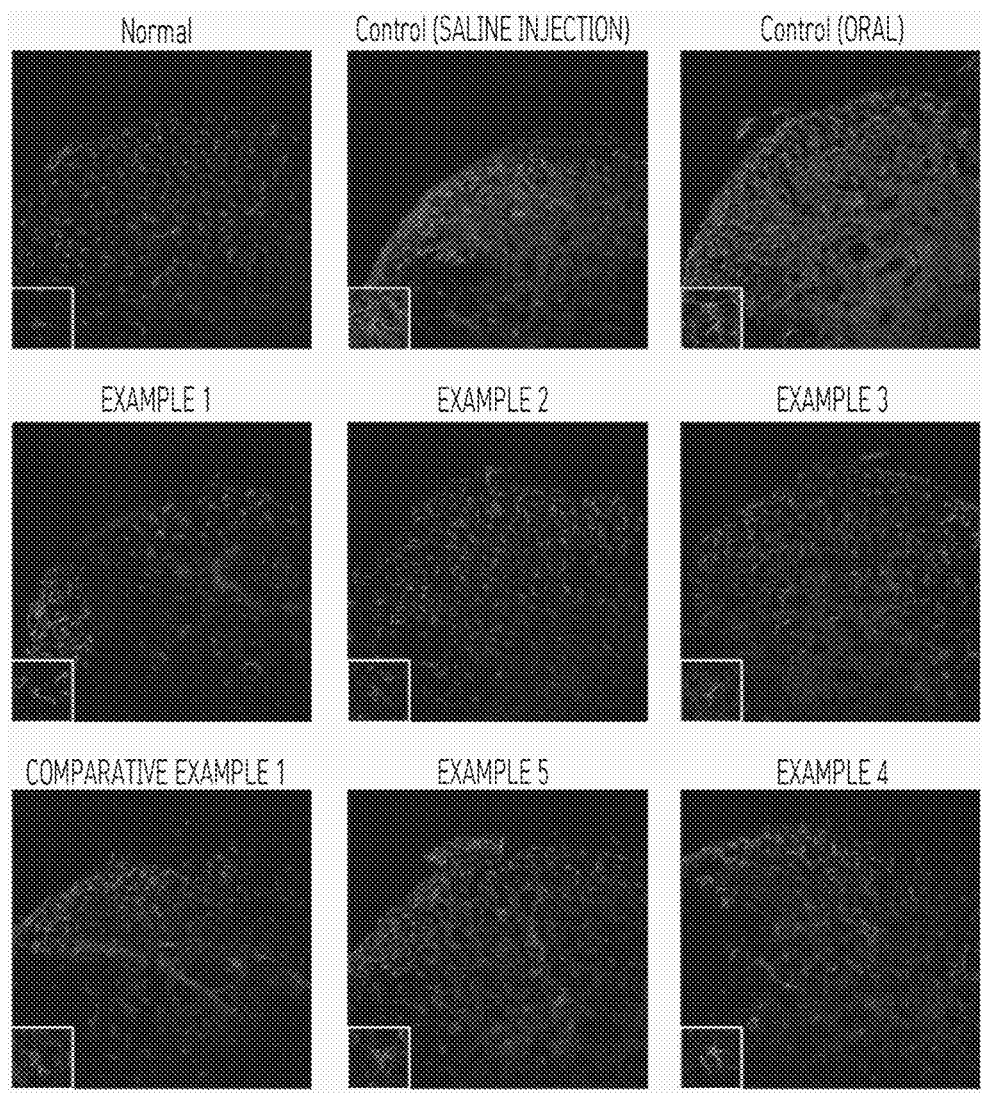
FIG. 5A shows images showing the effect of inhibiting the expression of GFAP in the spinal nerves by repeated administration of the compositions according to Examples 1 to 5 and Comparative Example 1.
Figure 5B:
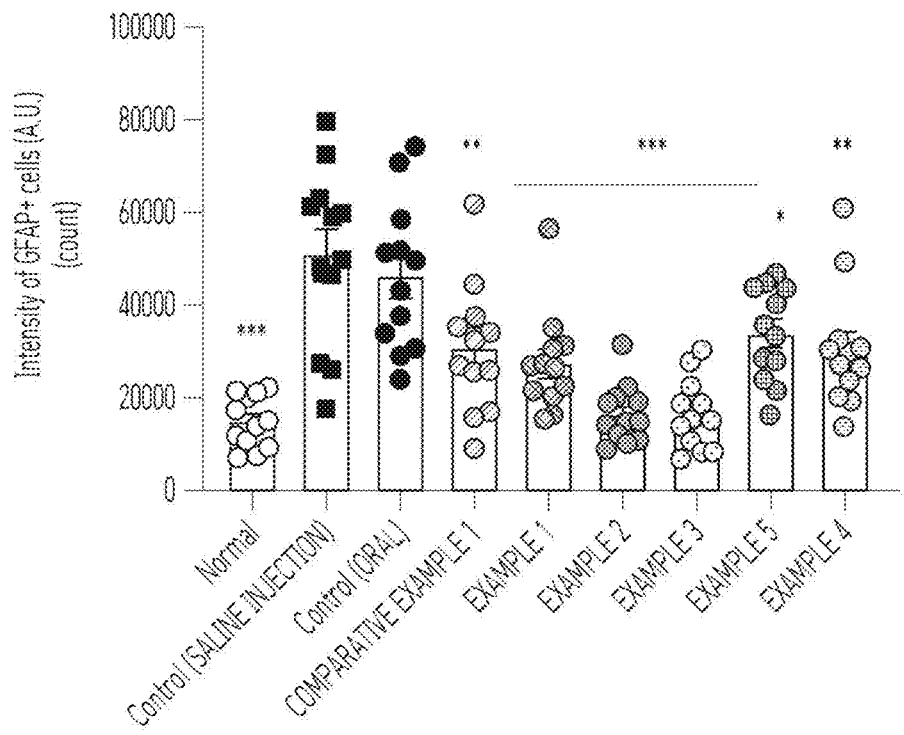
FIG. 5B is a graph showing the intensity of GFAP positive cells.
Figure 5C:
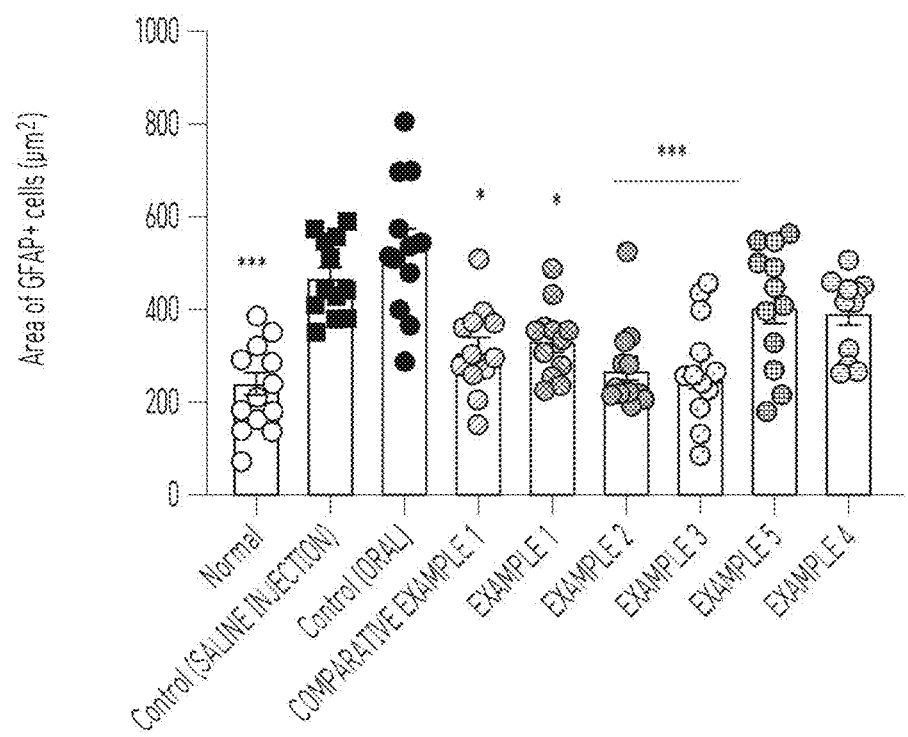
FIG. 5C is a graph showing the areas of GFAP cells.

FIG. 5A shows images illustrating the effect of inhibiting the expression of GFAP in the spinal nerves by repeated administration of the compositions according to Examples 1 to 5 and Comparative Example 1, FIG. 5B is a graph illustrating the intensity of GFAP positive cells, and FIG. 5C is a graph illustrating the areas of GFAP cells.

Referring to FIGS. 5A to 5C, SNL significantly increased the expression intensity and area of GFAP protein in the spinal dorsal horn compared to the Normal group (vs. the Control group (saline injection) or the Control group (oral), $p<0.001$). The administration of the composition of Comparative Example 1 showed a slight decrease in GFAP expression and a decrease in astrocyte size compared to the Control group (saline injection) ($p<0.01$, $p<0.01$). The administration of the compositions of Examples 1, 2, and 3 significantly inhibited the expression of GFAP compared to the Control group (saline injection) ($p<0.001$), and it was confirmed that the expression of GFAP was reduced in a concentration-dependent manner. The size of astrocytes (inflammatory cells) was also increased due to SNL, but was significantly reduced by the administration of the compositions of Examples 1 to 3 ($p<0.05$, $p<0.001$). The expression of GFAP was statistically significantly reduced compared to the Control group (saline injection) due to the administration of the composition of Example 5 ($p<0.05$). The expression of the composition of Example 4 for oral administration also statistically significantly reduced the expression of GFAP ($p<0.05$).

Experimental Example 4—Experiment on Anti-Inflammatory Effect

In order to confirm the activity of inflammatory cells and the expression of inflammatory cytokines in spinal nerves due to SNL, the expression of the astrocytes marker GFAP and the microglia marker Iba1 was confirmed through qPCR in spinal dorsal horn tissue ipsilateral to the damaged sciatic nerve.

Figure 6A:
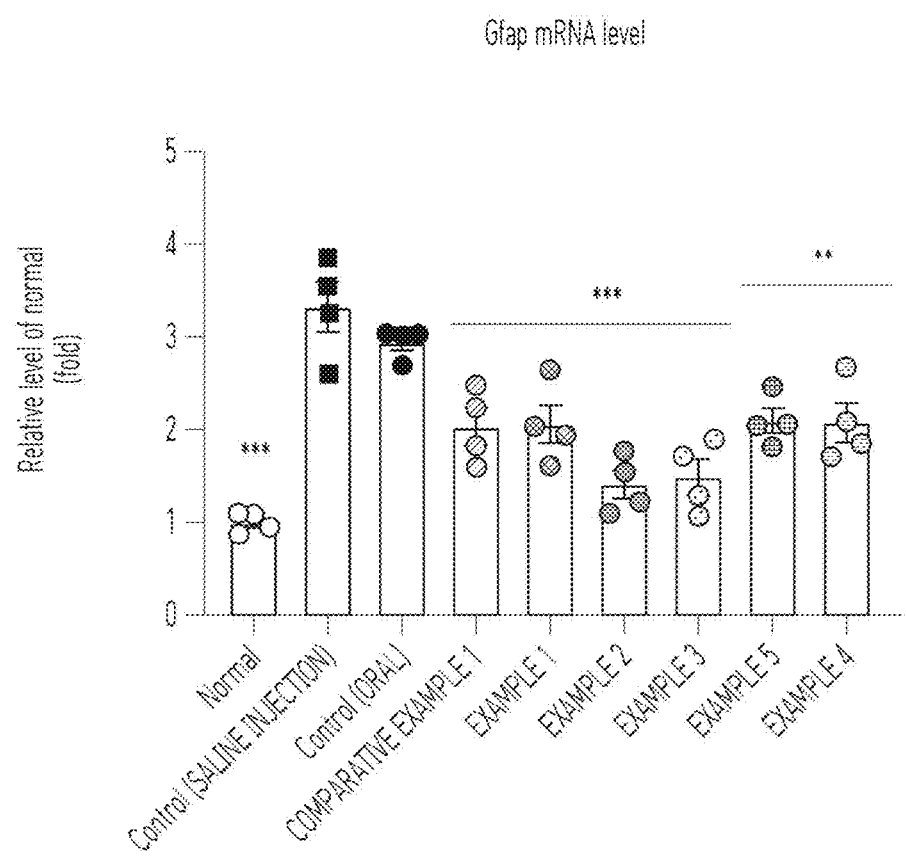
FIG. 6A is a graph showing the changes in mRNA level of Gfap by administration of the compositions according to Examples and Comparative Example.
Figure 6B:
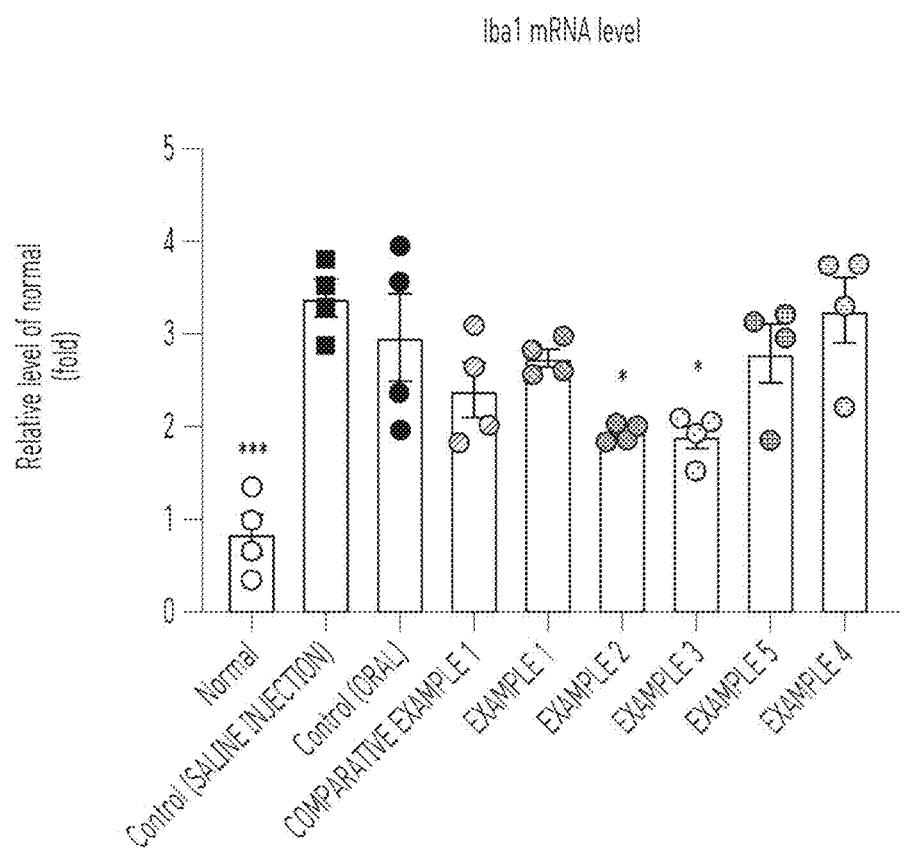
FIG. 6B is a graph showing the changes in mRNA level of Iba1 by administration of compositions according to Examples and Comparative Example.

Inflammatory cell markers GFAP and Iba1 were statistically significantly increased in the Control group (saline injection) compared to the Normal group ($p<0.001$). GFAP showed a significant decrease in all groups administered with the compositions (see FIG. 6A, $p<0.01$, $p<0.001$). In the case of Iba1, there was a significant decrease in the groups administered with the compositions of Examples 2 and 3 (see FIG. 6B, p<0.05).

Figure 6C:
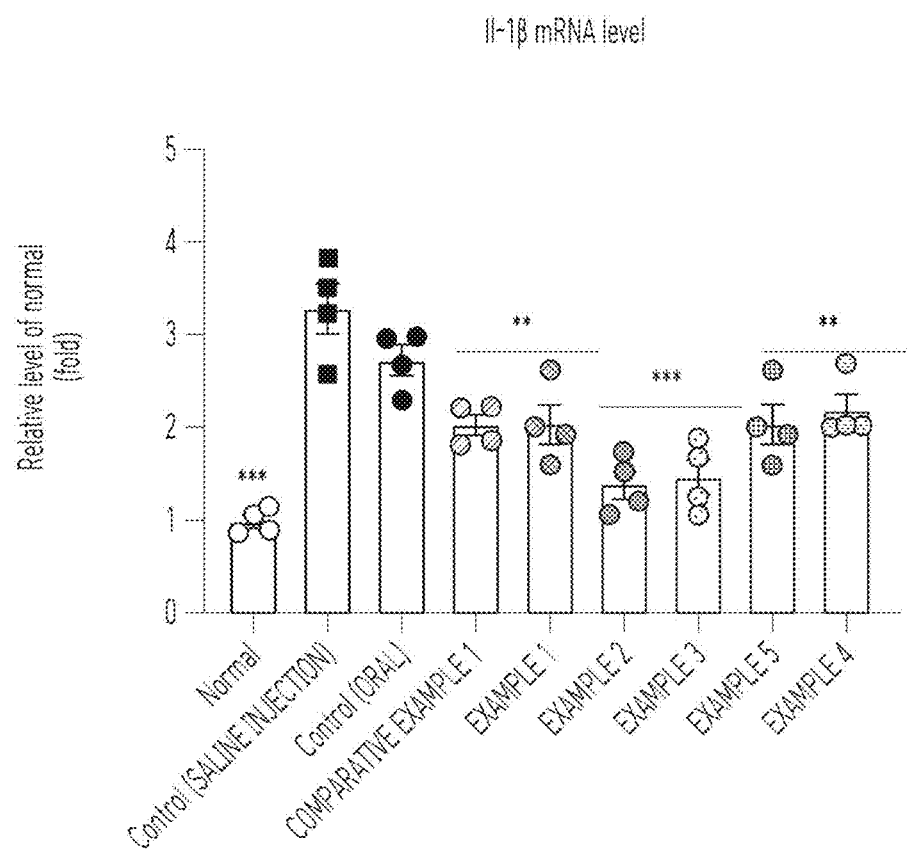
FIG. 6C is a graph showing the changes in the mRNA level of Il-1β by administration of the composition according to Examples and Comparative Example.
Figure 6D:
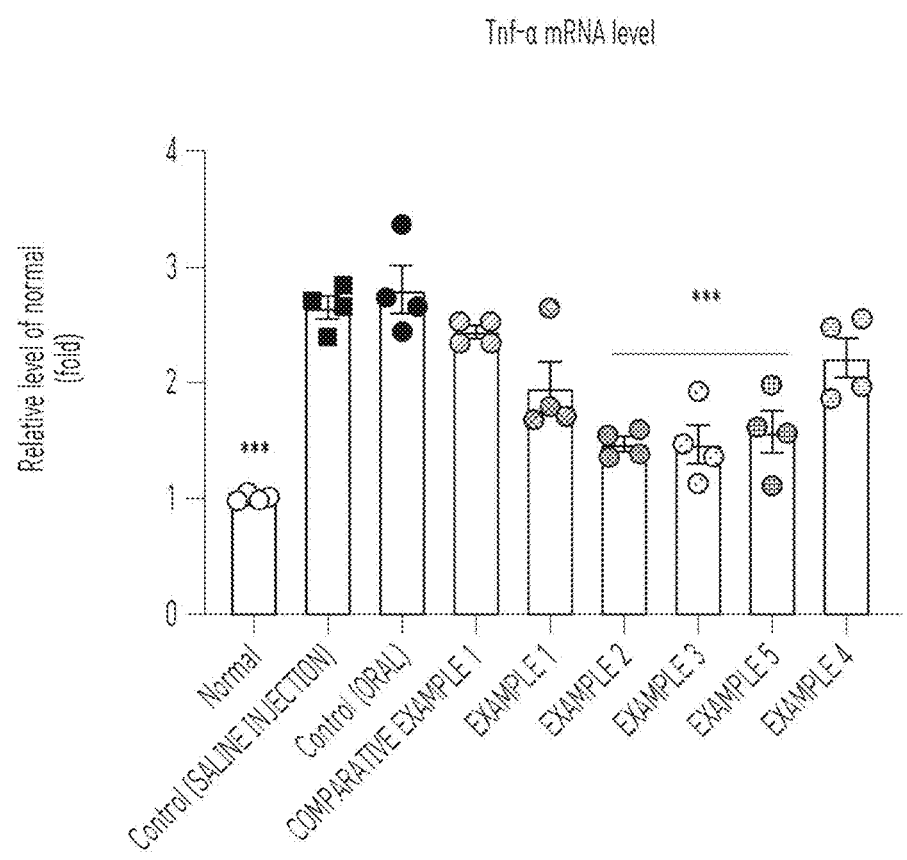
FIG. 6D is a graph showing the changes in mRNA level of Tnf-α by administration of the compositions according to Examples and Comparative Example.

In order to confirm the expression of inflammatory cytokines in spinal nerves due to SNL, the expression of the inflammatory cytokine markers Tnf-α and I1-1β was confirmed through qPCR in spinal dorsal horn tissue ipsilateral to the damaged sciatic nerve. The inflammatory cytokine marker I1-1β was statistically significantly increased in the Control group (saline injection) compared to Normal group (p<0.001). I1-1β showed a significant decrease in all groups administered with the compositions (see FIG. 6C, p<0.01, p<0.001). The expression of Tnf-α showed a significant decrease in the group administered with the compositions of Examples 2, 3, and 5 (right of FIG. 6B, p<0.001).

Summarizing the effects of the oral administration of the pharmaceutical composition according to Example 4, when compared with the Control group (oral), there was a statistically significant difference on day 10 and day 14 day after repeated administration (p<0.05, see FIG. 3A). In addition, when the pain level before administration was normalized to 100% and compared, a statistically significant analgesic effect was shown on day 10, day 12, and day 14 (p<0.05, p<0.01, p<0.001, see FIG. 3B). In addition, when compared with the Control group (oral), the expression of C-FOS in the spinal dorsal horn was significantly decreased (p<0.01, see FIGS. 4A and 4B), and the expression of GFAP was statistically significantly reduced compared to the Control group (oral) (p<0.05, see FIGS. 5A to 5C).

The pharmaceutical composition and pharmacopuncture composition according to an embodiment of the present disclosure may be effective in preventing, improving, or treating neuropathic pain, and may have an excellent anti-inflammatory effect.

Although the preferred embodiments of the present disclosure have been described in detail above, the scope of rights of the present disclosure is not limited thereto, and various modifications and improvements by those skilled in the art using the basic concept of the present disclosure defined in the following claims can also be made and they also fall within the scope of the right of the present disclosure.

What is claimed is:

1. A pharmaceutical composition for treating or preventing neuropathic pain comprising an extract of mixed herbal medicine comprising *Polygonati rhizoma, Sorbus commixta* Hedl., *Geranium nepalense, Glycine Semen Preparata* and *Imperata cylindrica* as an active ingredient.

2. The pharmaceutical composition of claim 1, wherein the pharmaceutical composition is a formulation of a preparation for oral administration.

3. A pharmaceutical drug for preventing or treating neuropathic pain comprising the pharmaceutical composition of claim 1.

4. A pharmacopuncture composition for treating or preventing neuropathic pain comprising the pharmaceutical composition of claim 1.

5. A pharmacopuncture composition for treating or preventing neuropathic pain comprising the pharmaceutical composition of claim 1, wherein the concentration of the extract of mixed herbal medicine comprising *Polygonati rhizoma, Sorbus commixta* Hedl., *Geranium nepalense, Glycine Semen Preparata* and *Imperata cylindrica* is 0.015 g/mL to 0.03 g/mL.

* * * * *